(12) United States Patent
Detalle et al.

(10) Patent No.: US 6,532,068 B2
(45) Date of Patent: Mar. 11, 2003

(54) METHOD AND APPARATUS FOR DEPTH PROFILE ANALYSIS BY LASER INDUCED PLASMA SPECTROS COPY

(75) Inventors: Vincent Detalle, Montreal (CA); Mohamad Sabsabi, Boucherville (CA)

(73) Assignee: National Research Council of Canada, Ottawa (CA)

( * ) Notice: Subject to any disclaimer, the term of this patent is extended or adjusted under 35 U.S.C. 154(b) by 0 days.

(21) Appl. No.: 09/906,061

(22) Filed: Jul. 17, 2001

(65) Prior Publication Data

US 2003/0016353 A1 Jan. 23, 2003

(51) Int. Cl.⁷ .................................................. G01J 3/30
(52) U.S. Cl. ........................ 356/318; 356/317; 356/36; 219/121.76
(58) Field of Search ................................ 356/318, 317, 356/36; 438/16, 14; 219/121.76, 121.77; 250/372

(56) References Cited

U.S. PATENT DOCUMENTS

| | | | |
|---|---|---|---|
| 5,751,416 A | 5/1998 | Singh et al. ................ 356/311 |
| 6,008,897 A | * 12/1999 | Sabsabi et al. ............. 356/318 |
| 2002/0104831 A1 | * 8/2002 | Chang et al. ............. 219/121.7 |

FOREIGN PATENT DOCUMENTS

WO  WO 88//01379  2/1988
WO  WO 00/08446  2/2000

OTHER PUBLICATIONS

"Depth profiling of tin–coated glass by laser ablation inductively coupled plasma emission spectrometry with acoustic signal measurement", Viktor Kanicky et al., Fresenius J. Anal. Chem.,2000, pp. 228–233.

"Depth–resolved analysis of multilayered samples by laser-–induced breakdown spectrometry", Jose M. Vadillo et al., Journal of Analytical Atomic Spectrometry, Aug. 1997, vol. 12, pp. 859–862.

* cited by examiner

Primary Examiner—Cassandra Spyrou
Assistant Examiner—Denise S. Allen
(74) Attorney, Agent, or Firm—Marks & Clerk

(57) ABSTRACT

In a method of spectrochemical depth-profile analysis of heterogeneous materials, a first burst of ablation laser pulses in a first beam is directed at a sample to form an ablation crater. A second single pulse or burst of laser pulses in a second beam having a smaller width than said first beam is then directed at the bottom of the crater so as to create a plasma that emits radiation representative of a component in the sample without a significant contribution from the walls of the ablation crater. The intensity of radiation from the plasma is measured and the concentration of the selected component is determined from the intensity of the radiation. The depth at which the measurement is taken is then evaluated and the above steps repeated to determined the evolution of concentration of said selected component as a function of depth.

32 Claims, 5 Drawing Sheets

METHOD AND APPARATUS FOR DEPTH PROFILE ANALYSIS BY LASER INDUCED PLASMA SPECTROS COPY

BACKGROUND OF THE INVENTION

1. Field of the Invention

This invention relates to optical instrumentation, and more particularly to a method and apparatus for depth profile analysis of materials by laser-induced plasma spectroscopy (LIPS).

2. Brief Description of the Prior Art

Coatings and surface modification by the diffusion of elements into materials are widely used in industry to give enhanced properties to the materials. A knowledge of the compositional variation in surfaces and interfaces is of primary interest since interfacial composition plays a key role in the functional behavior of the material. The quality of these layers can be investigated by a number of techniques depending on the information required. Classical analytical chemistry has focused on techniques and methods giving information on bulk composition and few are devoted to depth profiling. Techniques such as Auger and X-ray photoelectron spectroscopy have been used to study surface chemistry on the atomic scale, and can be used to probe into the coating by removing material through ion bombardment to yield depth profile data. Thicker coatings can be analyzed with the use of X-ray spectrometry and Rutherford backscattering techniques. However, such techniques require working in ultra-high vacuum conditions to avoid scattering by molecules in the gas phase, a circumstance that imposes severe restrictions on the practical use of these approaches. Glow discharge optical emission spectrometry (GD-OES) and glow discharge mass spectrometry (GD-MS) have been used to measure coatings over a thickness range 0.01 $\mu$m to over 50 $\mu$m. Measurement times are about 15 minutes and depth resolution is typically around 100 nm. These techniques suffer from poor lateral resolution. Furthermore the specimen shape and thickness is limited to the sample chamber configuration.

These and other conventional techniques used in industry for depth profile analysis require preparation of the sample, are time consuming, and involve high cost instrumentation (e.g. Auger, GD-MS). Furthermore, some techniques based on X-ray fluorescence are also limited in sensitivity.

An emerging method, laser-induced plasma spectroscopy (LIPS), promises to provide rapid, in-situ compositional analysis of a variety of materials in hostile environments and at a distance. Basically, this method includes focusing a high power pulsed laser beam on the material, thus vaporizing and ionizing a small volume of the material to produce a plasma having an elemental composition which is representative of the material composition. The optical emission of the plasma is analyzed with an optical spectrometer to obtain its atomic composition.

The great need in industry for fast techniques with on-site capabilities makes LIPS a promising technique for in depth profile analysis of layered materials. However, the energy distribution within the laser beam (typically a near Gaussian mode in many laser systems) has limited the depth resolution achievable with this technique as it produces cone-shaped craters with non-negligible edge contribution to the ablated mass. Several solutions have been proposed to remedy this problem. Vadillo and Laserna (J. Anal. At. Spectrometry, vol. 12, 1997, p. 859) improved the depth resolution of LIPS measurements by using a simple two-lens telescope combined with a pinhole mask to generate a collimated output of a XeCl excimer laser, resulting in a flat energy profile. Beam masking has also been employed to attenuate the shot energy and to eliminate the peripheral irregularity of the beam profile (by Kanicky et al., Fresenius J. Anal. Chem., vol. 336, 2000, p. 228). These approaches have solved, to some extent, the problem of irregular energy distribution over the beam cross section but have failed to eliminate the interaction between the laser and the wall of the crater. In fact, the plasma produced by the laser also interacts with the wall of the crater and induces some mixing of material, which complicates the analysis by LIPS, in particular in the region close to an interface.

An object of this invention is to provide a tool to overcome this problem and make it possible to realize a measurement without being affected by the edge of the crater.

It is also an object of this invention to enhance the resolution of depth profiling by LIPS. The basics of this technique are known in the art for analysis of elements present in a sample and is described, for example, in U.S. Pat. No. 5,751,416, the contents of which are incorporated herein by reference.

SUMMARY OF THE INVENTION

An object of our invention is to provide a reliable depth profile analysis of solid material. Accordingly, this invention consists in a new method and apparatus for measuring the evolution of concentration as a function of depth and can achieve a more accurate measurement than classical instrumentation, without sample preparation.

The present invention features two different probes. The same laser generates the two probes. The first probe produces a reproducible and controlled ablation that produces a first large crater and the second probe, collinear with the first, has a smaller beam size and allows generating the analytical plasma inside the crater. The emission of the plasma is collected and separated in an optical spectrometer.

Accordingly in a first aspect the present invention provides a method of spectrochemical depth-profile analysis of heterogeneous materials, comprising directing a first burst of ablation laser pulses in a first beam at a sample to form an ablation crater with a bottom and wall; directing a second single pulse or burst of laser pulses in a second beam having a smaller width than said first beam at the bottom of said crater so as to create a plasma that emits radiation representative of a component in the sample without significant contribution from the wall of the ablation crater, measuring the intensity of radiation from said plasma; determining the concentration of said selected component in said material from the intensity of said radiation; and evaluating the depth at which said plasma is created. The above steps are preferably repeated in order to determine the evolution of concentration of the selected component as a function of depth.

Many laser systems produce a near-Gaussian energy distribution within the laser beam, which limits the depth resolution achievable with the LIPS technique as it produces cone-shaped craters with a non-negligible peripheral contribution to the ablated mass. The first part of this invention allows obtaining a more homogenous ablation by using only the center of the laser beam. The laser shot number controls the ablation depth. The second part of this invention allows performing an analysis of the surface at the bottom of the crater, without any contribution from the crater wall.

In one aspect of this invention, there is provided an apparatus for depth spectroscopic analysis of heterogeneous materials, comprising an energy source for generating pulses of energy in the form of a first beam of predetermined width incident on a sample to cause ablation thereof and thereby form a crater with a bottom and a wall; an energy source for generating a single pulse or burst of pulses in a second beam of laser light, said second beam having a width less than said first beam and being directed at the bottom of said crater so as to form a plasma emitting radiation representative of a selected component present in said material without significant contribution from the wall of the crater; a detector for measuring the intensity of radiation of said selected component at different depths of crater; and a depth profile evaluator for determining the depth of the crater for each radiation intensity measurement.

The energy sources can be one or two lasers disposed such that their optical paths are substantially collinear. A small deviation from colinearity is acceptable.

The measuring device, e.g. a spectrometer, is preferably disposed substantially colinearly with the optical path of the laser beams.

The dimensions of the laser beam at the focal point is not a significant factor. The beam used for ablation must simply be larger than that used to carry out the measurement. Typically, a diameter ratio of 1/3 could be used.

BRIEF DESCRIPTION OF THE DRAWINGS

The objects, features and advantages of the present invention will become apparent from the following detailed description of the invention in conjunction with the drawings in which.

DETAILED DESCRIPTION OF THE PREFERRED EMBODIMENTS

In accordance with the principles of the invention two laser pulses or bursts of laser pulses of different diameter are used. The first laser pulse or burst (the number of laser shots determine the resolution of depth profiling) realizes the ablation. The second laser pulse or burst (the number of laser shots increases the precision) vaporizes a small volume at the bottom of the crater generated by the first laser pulse or burst, and produces plasma of which the optical emission is analyzed with a spectrometer. The spectrum is detected through appropriate optics by a gated photodiode array detector, an intensified CCD camera, or by an array of photomultipliers each individually positioned to detect an emission line representative of a given element.

The material may be opaque or partly transparent. As a result of the high temperature generated, a small amount of the material is ablated, vaporized and ionized, its atoms and ions being brought in excited states, thus allowing species in the plasma to be identified by spectrally and temporally resolving the spark light emission.

Figure 5:
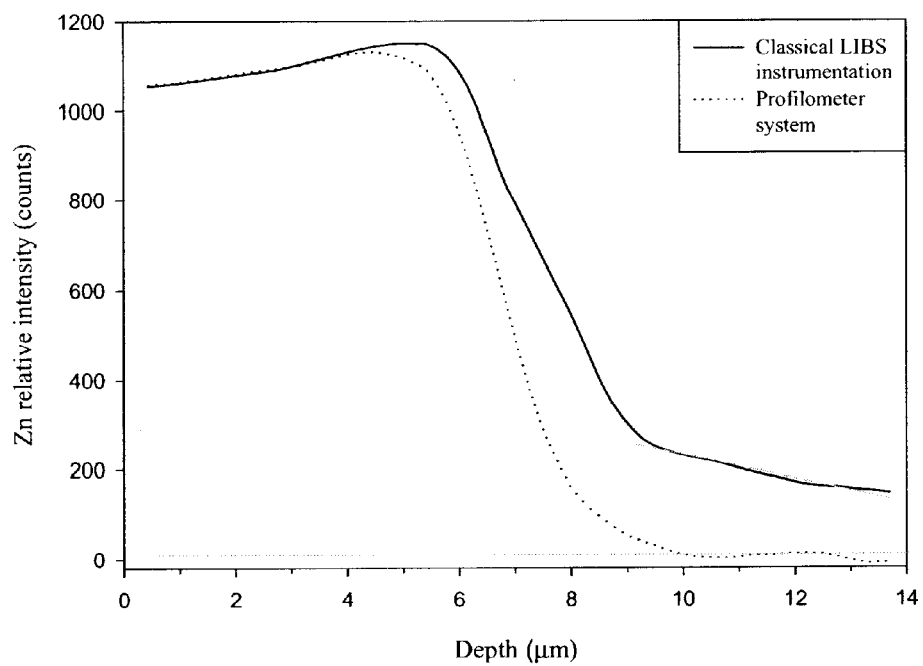
FIG. 5 shows two depth profiles of the zinc emission line obtained with classical LIPS instrumentation and by using the method and apparatus of the present invention.

To perform a reliable depth profile analysis, it is important to ensure a controlled and reproducible ablation rate and a well-characterized ablation volume. The ablation has to be the same for each shot in terms of radial distribution of the ablated depth. In order to obtain this result, the spatial characteristics of the laser beam have to be controlled and the laser needs to be stable from shot to shot. Furthermore, to achieve a good depth resolution, all parts of the laser beam throughout its cross-section should sample the material at approximately the same depth. This condition is difficult to satisfy with a near-Gaussian laser beam, which produces cone-shaped craters. Inevitably, for any given shot (except the first), the laser will sample material from different depths along the crater surface. In view of this, it seems clear that modification of the energy radial distribution of the laser beam should be developed to increase the depth resolution. To do so, a diaphragm is used to select only a homogenous part of the laser beam. A homogenizer could be added before the diaphragm to this set-up in order to obtain a better laser beam profile. This setup allows a better control of the generated crater shape. However, in spite of this technical improvement, the optical emission of the plasma always shows a non-negligible contribution from the wall of the crater. This degrades the precision of the result, and in particular increases the apparent spatial extent of the transition in composition between a coating and a substrate as shown in FIG. 5.

To overcome this problem, a second smaller laser beam (the analyzing beam) is focused inside the crater, and generates plasma emission, which is only dependent on the composition of the bottom of the crater. The role of the second beam is to probe in a very precise way the elementary composition of the thinnest zone also possible without contribution from the edge of the crater. The depth resolution also depends on the number of ablation shots in the first step, the energy in this laser beam, the wavelength of the laser, and can be adjusted according to the needs or the nature of the samples.

Generally the number of ablation shots will be much higher than the number of analyzing shots, typically 100 to one. The depth of the small crater generated by the analyzing beam can be neglected compared to the depth of the ablation crater. However, when high resolution is needed the ratio of ablation shot number to the analyzing one could be less than 100. This means the highest resolution corresponds to a ratio of one, i.e. one ablation shot is followed by an analyzing shot. The depth of crater produced by analyzing shot cannot be neglected. To overcome this problem, different solutions are possible. First, the energy of the analyzing pulse can be reduced in order to avoid the surface damage. If the emission signal of the analyzing plasma resulting from the laser pulse is too weak, the plasma can be excited with a second laser pulse (U.S. Pat. No. 6,008,897) at appropriate wavelength which could be generated by a wavelength tunable laser source. Secondly, a mixed-wavelength pulse can be used as analyzing beam shot (Patent pending). The use of mixed-wavelength laser pulse damages less the surface because of the screening and plasma absorption.

Figure 1:
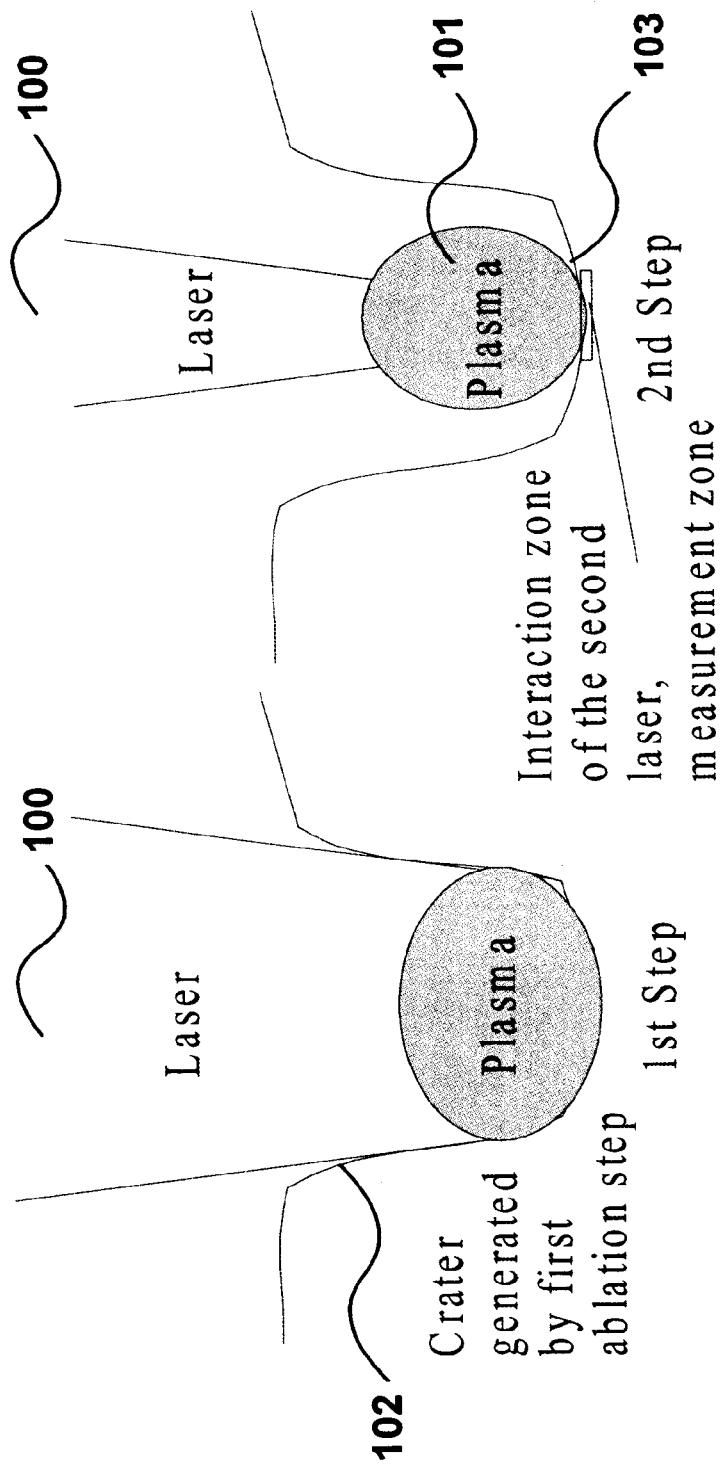
FIG. 1 illustrates the principle of operation of the invention.

As shown in FIG. 1, an ablation beam 100 produces a plasma at the bottom of the crater 102 generated in a first ablation step. A second laser beam which has smaller diameter is used to make a measurement in the interaction zone 103 at the centre of the bottom of the crater and produces a second plasma. The emission of this plasma 101 is analyzed in order to obtain the composition of the interaction zone without contribution of the crater edge.

Figure 2A:
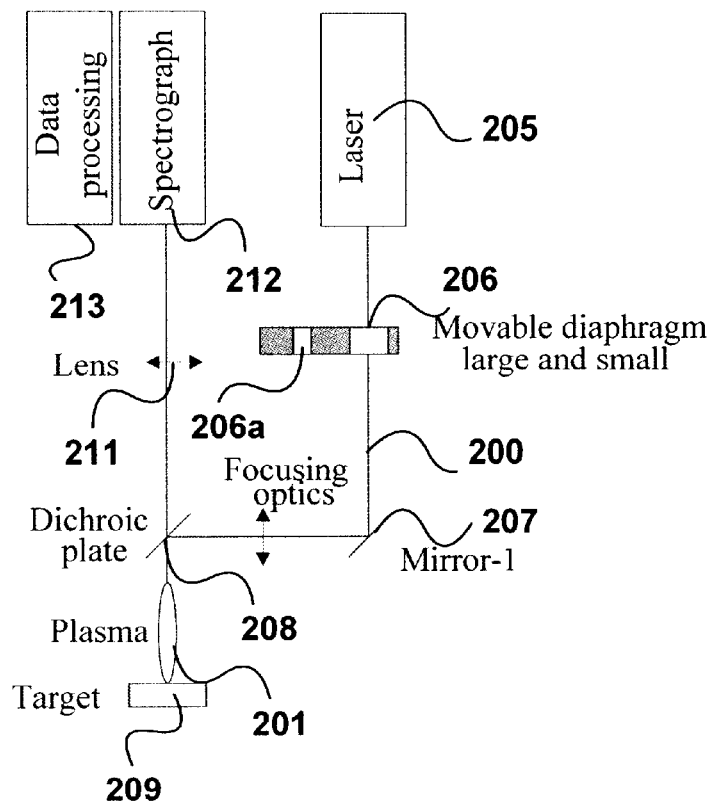
FIGS. 2a to 2c are overall block diagram of various embodiments of the invention.
Figure 2B:
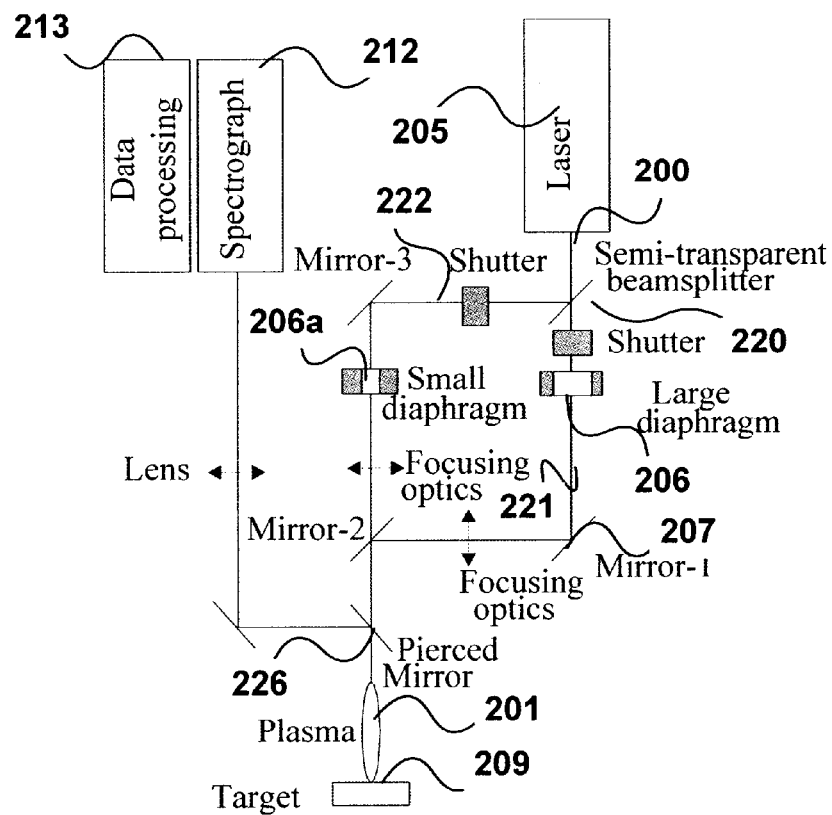
Figure 2C:
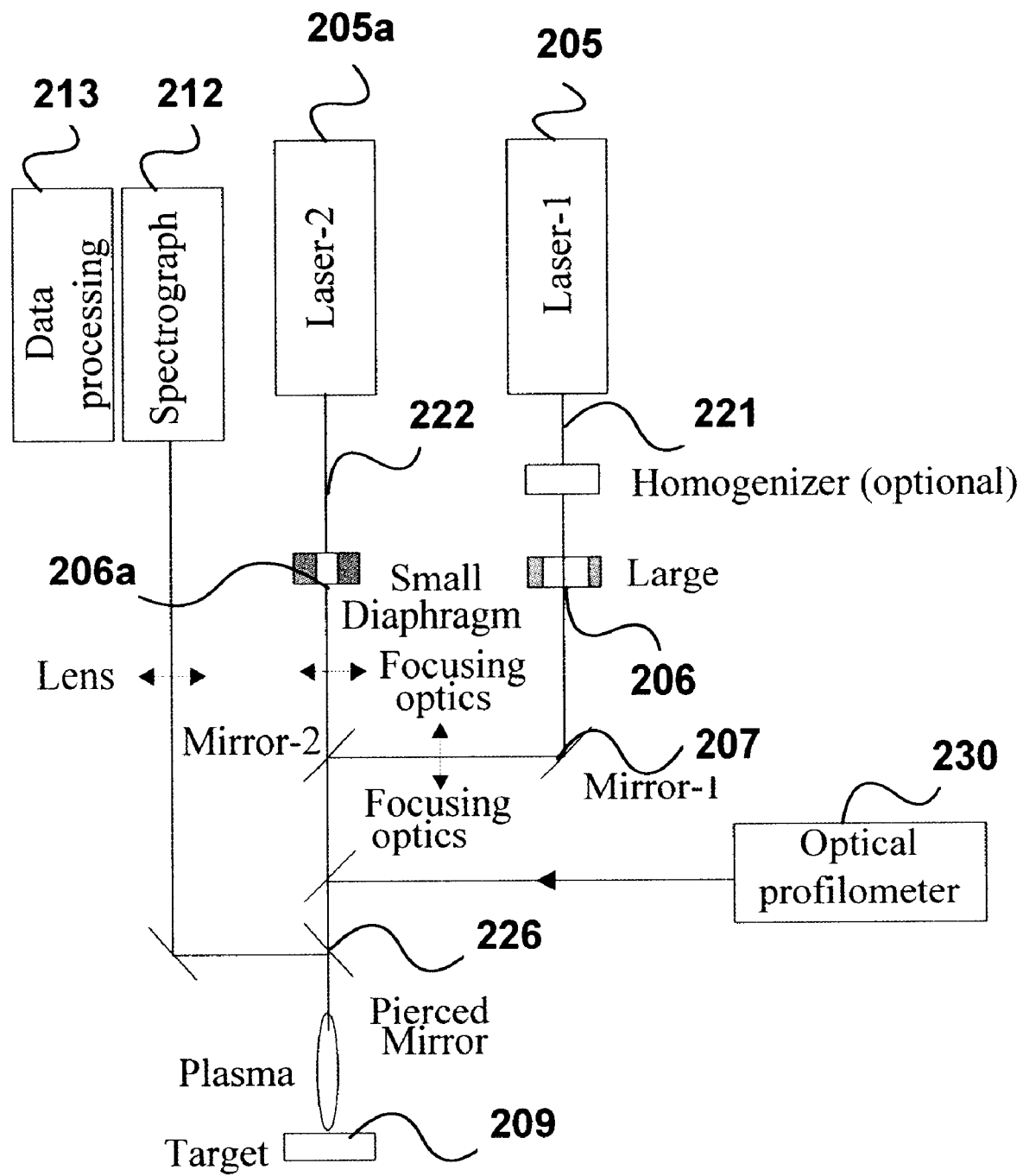

FIGS. 2a to 2c show three different experimental setups all built on the same principle.

In the embodiment shown in FIG. 2a, just one laser 205 is employed and the laser beam 200 passes through a large diaphragm 206 and is reflected by a mirror 207 through focusing optics and reflected by a dichroic plate 208. A crater is formed on the target 209 by focusing the laser beam 200 using a focusing system ideally composed preferably of two lenses in order to realize an image of the diaphragm on the surface with a chosen magnification. A counter (not shown) allows firing a predetermined number of shots to control the ablation depth. Then, a movable diaphragm support (not shown) is actuated and the smallest diaphragm 206a is moved in the place of the large diaphragm 206 on the same optical axis. This allows a measurement, to be made at the center of the first crater. The diaphragm material is preferably made of a light scattering material and low absorption material at the laser wavelength, in order to increase the lifetime of this component.

With the aid of a lens 211, a reduced image of the plasma is created at the entrance slit of the spectrometer 212, which is connected to a data processing unit 213. The current configuration thus allows efficient collection of the light emitted by the plasma along the axis of the plasma plume using a dichroic plate, or a pierced mirror. The optical emission from the plasma is spectrally analyzed using typically a grating spectrometer equipped with a gated detector such as an intensified photodiode array detector, CCD camera, or an array of photomultipliers each individually positioned in the focal plane to detect, simultaneously and during a specified time period, a number of emission lines representative of the different elements in the material to be analyzed. Standard techniques are used to properly synchronize the lasers and detectors so as to collect the emission signal during the time window providing the best signal to noise ratio, while a fast computer evaluates the measured spectra and calculates the element concentrations via calibration procedures which are well known to spectroscopists.

The set-up shown in FIG. 2b includes two optical paths. A 50/50 beamsplitter 220 is located immediately downstream of the laser 205. The laser beam in this setup follows the first optical path 221 (the second path 222 is stopped by a shutter), and as in the first setup, it passes through a large diaphragm 206 and is reflected by a mirror 207. A crater is formed on the target by focusing the laser beam using a focusing system ideally composed preferably of two lenses in order to realize an image of the diaphragm on the surface with a chosen magnification. A counter allows firing a predetermined number of shots to control the ablation depth. After this first step, a shutter stops the ablation laser beam 221 and the shutter 225 is opened, in order to allow the beam to follow the second path. The same results could be obtained using an electro-optic cell with beam splitter 220 being a polarizing beam splitter. Such a device would be located immediately after the laser output, and by application of a controlled voltage will shift the polarization so the laser beam is sent either along path 221 or 222. Then, in this new path is disposed a smaller diaphragm 206a coupled to a focusing system that focuses the laser beam into the first crater. A polarized beamsplitter located in this path (mirror-2) reflects the first beam and lets pass the second beam when the electro-optic system is used (half wave plates are used in both paths to flip the polarization). Otherwise, a 50/50 plate replaces it. For this setup, a pierced mirror 226 is required. The detection device is identical to the first setup.

The third configuration shown in FIG. 2c permits a similar result to be obtained using two lasers 205, 205a. The first laser beam follows exactly the same path that is described in setup (b), and controls the ablation step. A beam homogenizer could be used in order to obtain a better laser beam profile. The second laser 205a is used in the measurement step, and it is positioned in order to be focused at the center of the bottom of the crater generated by the first laser. For this setup, the use of a diaphragm and a focusing system as already described is preferable but not obligatory, a simple lens can replace the diaphragm and focusing system. The only requirement is that the diameter on the target surface of the laser beam 221 is larger than laser beam 222 at the same position. For this setup, pierced mirror 226 is used as collection tool, and the detection arrangement is identical to the other setups. This embodiment shows also that an optical profilometer is integrated with the system and is used to monitor throughout the whole analysis the depth of the crater. Preferred configurations of such a profilometer are shown in FIGS. 3a and 3b.

Independently of the configuration used for the LIPS system, in order to perform accurate profilometry, the depth at which each measurement is made has to be evaluated. This evaluation can be performed by taking the sample off the LIPS system and measuring the crater depth with a profilometer. The profilometer can be based on confocal microscopy, laser triangulation or interferometry using a short coherence length light source (also called white light interferometry or optical coherence tomography). In confocal microscopy, light is sent through a pinhole and the light collected through the same pinhole after reflection by the object is monitored. The surface location is determined by noting that the collected light is at maximum when the image of the pinhole is at focus on the surface. In laser-triangulation, the light spot at the surface of the object is viewed by a linear camera along a direction making an angle with the illumination axis. The position of the spot on the linear camera is dependant upon the distance of the surface from the device, which allows monitoring the surface location. In interferometry with a short coherence length source, a maximum interference signal is observed when the path length along the arm going to the object is equal to that a reference arm whose length is varied. This variation being calibrated, this technique also allows monitoring the surface location.

Crater depth measurement for each composition analysis (or after a certain number of analyses) requires positioning the sample at the same location under the LIPS apparatus, which is possible, but generally inconvenient. In some cases, it is also possible to calibrate the ablation rate so only one measurement is needed at the end of analysis. For example for a layer on top of a substrate, a depth measurement can be performed on calibration samples with a layer on top and without a layer. From these measurements, the removal rate per laser shot in the layer and in the substrate is evaluated. From this calibration, count of the laser shots and final depth measurement, the depths in the homogenous zones are readily evaluated. Depth in the transition zone is performed with a reasonable accuracy by interpolation. This obviously assumes that the ablation rate is the same for the study sample and the calibration samples, which in particular requires sufficient laser stability (total power and power distribution). Furthermore such a procedure is not applicable on samples with composition variation right from the surface or more complex multi-layer samples. Consequently, it will be much convenient to have the depth measurement provision integrated with the LIPS apparatus. The two following embodiments show how this can be accomplished by using interferometry with a short coherence length source.

Figure 3:
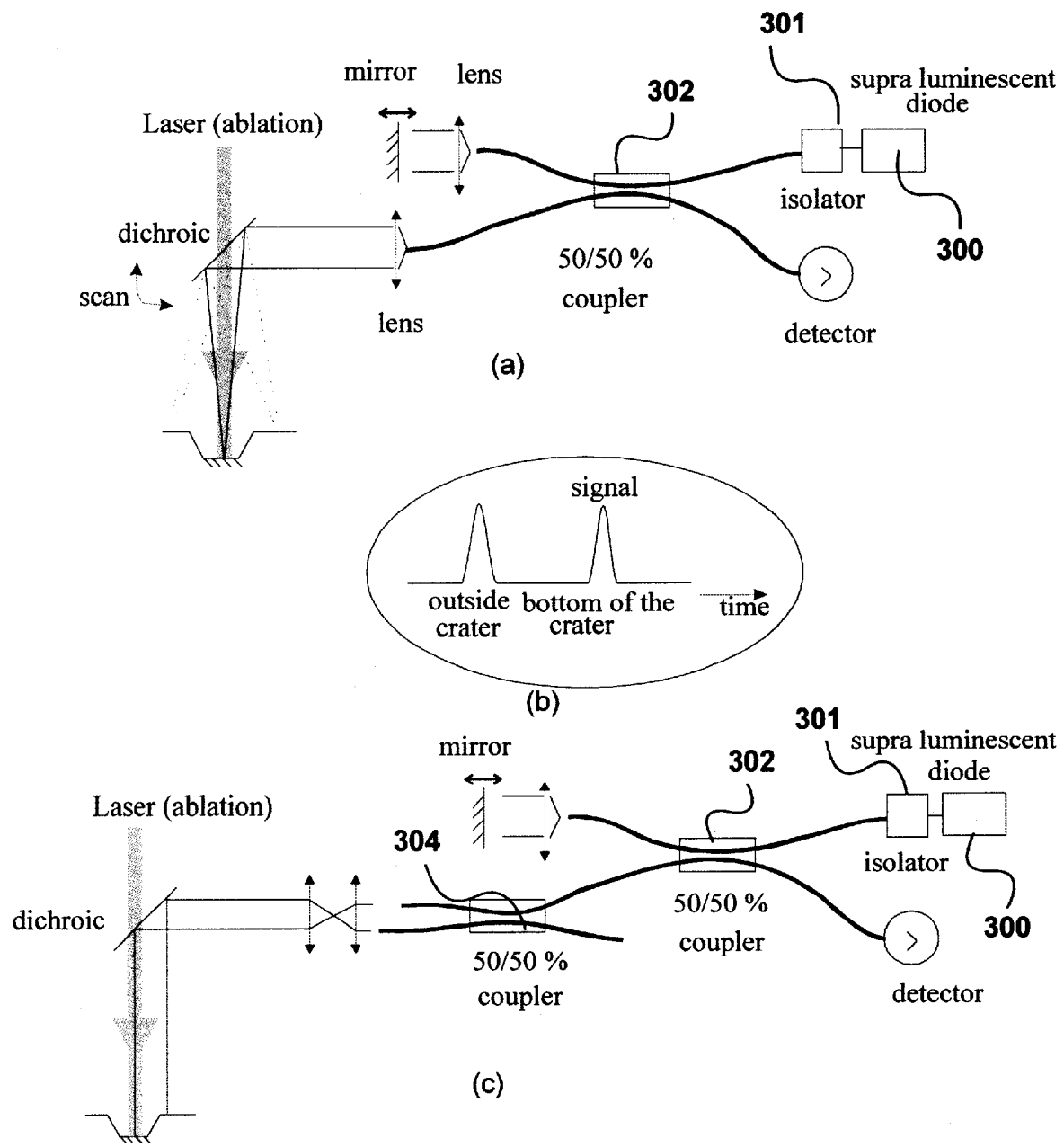
FIGS. 3a and 3c shows two possible embodiments of the depth measuring system based on interferometry with a short coherence length source.
FIG. 3b shows the envelopes of interference signals from which crater depth is determined.

FIG. 3a shows an embodiment which actually realize a two-wave Michelson interferometer made of single mode optical fibers. A supra luminescent diode 300 giving a bandwidth of typically 20 nm is used as light source. This diode 300 is followed by an optical isolator 301 to prevent feedback from any interface and from the surface of the object of affecting its operation. The beam is then fed through a splitter/mixer 302, which is a 50—50% bi-directionnal coupler. The reference arm length is varied by collimating the beam with lens and mounting the mirror (or a retroreflector) on a translation slide. In the arm going to the object, the beam emerging from the fiber is focused onto the surface by a lens and a dichroic mirror mounted on a rotating slide or a galvanometer. This dichroic mirror lets the ablation beams to go through, reflects the interferometer light and allows scanning across the crater. Assuming that the reference arm scan is much faster than the scan across the crater, depth information is obtained for each position across the crater from the signal observed at zero path length difference on the detector.

In the second and preferred embodiment, no scanning across the crater is performed and only two depth measurements are performed, one inside the crater at the location of elemental analysis and the other one outside the crater in a region unaffected by ablation and residual debris.

As shown in FIG. 3c, another 50—50% bidirectional coupler 304 is used in the arm going to the sample to give two secondary light sources that are separated by a given distance. A telecentric optical system made of two lenses is then used to focused them on the sample, one at the measurement location in the crater and the other one outside the crater.

FIG. 3b shows two signals (envelopes of the interference signal) from which the crater depth is determined, the scan of the reference arm being calibrated. The two secondary sources given by the second 50—50% coupler are not in the same plane so the two signals are conveniently separated before the start of any ablation.

Figure 4:
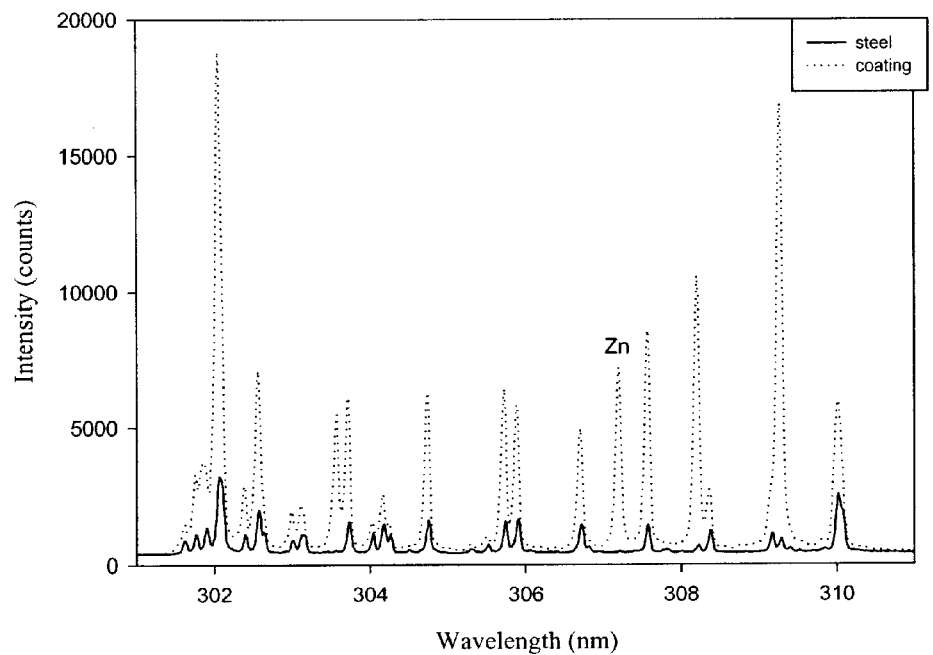
FIG. 4 shows two different emission spectra, one characteristic of the coating composition, and the second one characteristic of the substrate.

FIG. 4 shows spectra obtained with the apparatus of FIG. 2a by firing on a 1 mm diameter pinhole coupled to focusing optics (lens couple) allowing to obtain, 500 $\mu$m diameter spot (×2 demagnification) at the surface of an annealed galvanneal coated steel sample (containing approximately 9% of Fe in a Zn matrix). The first spectrum is obtained with a single shot of 60 $\mu$J energy on the zinc coating, and the other one after several ablation shots have reached the steel substrate (with Fe as main component). The comparison of the two optical emission spectra shows the disappearance of the Zn emission lines. This information is used to measure the thickness of the Zn coating.

FIG. 5 is a comparison of two depth profiles of zinc obtained by monitoring the 307.21 nm emission line. The ablation depth is evaluated by interferometry with a short coherence length source as described above. The sample is galvannealed steel annealed zinc-coated steel. The zinc coating has been analysed by electronic microprobe (reference analytical technique for the analysis of solids). The coating thickness is approximately 7 $\mu$m with an interface length between Zn/steel of less than 2 $\mu$m.

One of the profiles shown in FIG. 5 is obtained by using classical LIPS instrumentation, the laser beam being filtered by a large diaphragm. The second one is obtained using the present invention. In the two cases, each point of measurement corresponds to 10 measurement shots, after 100 ablation shots, obtained with the large diaphragm. It is seen that the profilometry technique according to the present invention provides a more accurate measurement of the coating thickness. The interface is described with more precision: the beginning of the interface appears in the same place with the two systems but ends 2 $\mu$m sooner with the system according to this invention. The Zn emission line falls down to zero quickly using this invention, which is not the case with conventional instrumentation where the Zn emission persists. The results of measured thickness and of interface length obtained with this invention are very close to those obtained with a conventional electronic microprobe.

The above description of the present invention is susceptible to various modifications, changes and adaptations, and the same are intended to be comprehended within the scope of the appended claims.

We claim:

1. A method of spectrochemical depth-profile analysis of heterogeneous material, comprising:
   a) directing a first burst of ablation laser pulses in a first beam at a sample to form an ablation crater with a bottom and wall;
   b) directing a second single pulse or burst of laser pulses in a second beam having a smaller width than said first beam at the bottom of said crater so as to create a plasma that emits radiation representative of a component in the sample without significant contribution from the wall of the ablation crater,
   c) measuring the intensity of radiation from said plasma;
   d) determining the concentration of said selected component in said material from the intensity of said radiation; and
   e) evaluating the depth at which said plasma is created.

2. A method as claimed in claim 1, wherein the steps a to e are repeated in order to determine the evolution of concentration of said selected component as a function of depth.

3. A method as claimed in claim 1, wherein said first and second beams are produced by passing a laser beam through diaphragms of different widths.

4. A method as claimed in claim 2, wherein a movable diaphragm support containing large and small diaphragms is located in a common laser beam, and said movable diaphragm support is displaced to bring respectively the large and small diaphragm into said common laser beam to create sequentially said first and second beams.

5. A method as claimed in claim 2, wherein said laser beam is passed through a beam splitter to generate said first and second beams, and a shutter is located in each said first and second beams to block one of said first and second beams while the other of said first and second beams is active.

6. A method as claimed in claim 3, wherein said first and second beams are produced by a respective first and second lasers, and said diaphragms are located in said first and second beams produced by said first and second lasers.

7. A method as claimed in claim 1, wherein said second pulse or burst of pulses are of mixed wavelength.

8. A method as claimed in claim 1, wherein said second pulse or burst of pulses are generated by a wavelength tunable laser.

9. A method as claimed in claim 3, wherein said first beam is homogenized with a homogenizer upstream of said diaphragm in said first beam.

10. A method as claimed in claim 9, wherein the depth is measured by a technique selected from the group consisting of: confocal microscopy, laser triangulation and interferometry using a short coherence length light source.

11. A method as claimed in claim 9, wherein the measurement of depth is enhanced by interpolation.

12. A method as claimed in claim 1, wherein the ablation rate is initially calibrated by measuring the depth after a known number of laser shots, and the calibrated ablation rate is then used to determine the depth in step e for subsequent measurements.

13. A method as claimed in claim 1, wherein the width of the second beam is about ⅓ the width of the first beam.

14. A method as claimed in claim 1, wherein said second beam is focused at the center of the bottom of said crater.

15. A method as claimed in claim 1, wherein the ratio of pulses of said first laser burst to said second laser pulse or burst is about 100:1.

16. An apparatus for laser-based spectrochemical depth-profile analysis of a heterogeneous material, comprising:

an energy source for generating pulses of energy in the form of a first beam of predetermined width incident on a sample to cause ablation thereof and thereby form a crater with a bottom and a wall;

an energy source for generating a single pulse or burst of pulses in a second beam of laser light, said second beam having a width less than said first beam and being directed at the bottom of said crater so as to form a plasma emitting radiation representative of a selected component present in said material without significant contribution from the wall of the crater;

a detector for measuring the intensity of radiation of said selected component at different depths of crater; and a depth profile evaluator for determining the depth of the crater for each radiation intensity measurement.

17. An apparatus as claimed in claim 16, wherein the energy source for producing said first beam and said energy source for producing said second beam are provided by a common laser generating an output beam, which is formed into said first and second beams.

18. An apparatus as claimed in claim 17, further comprising a beam splitter for forming said output beam into said first and second beams.

19. An apparatus as claimed in claim 18, comprising a first diaphragm in said first beam and a second diaphragm in said second beam, said second diaphragm having a smaller diameter than said first diaphragm.

20. An apparatus as claimed in claim 19, further comprising a shutter in each of said first and second beams to block one of said first and second beams while the other of said first and second beams is active.

21. An apparatus as claimed in claim 17, comprising first and second diaphragms, said second diaphragm having a smaller diameter than said first diaphragm, each of said diaphragms being locatable in said output beam to provide sequentially said first and second beams.

22. An apparatus as claimed in claim 20, wherein said first and second diaphragms are mounted on a displaceable support.

23. An apparatus as claimed in claim 16, wherein said energy source for producing said first beam and said energy source for producing said second beam are respectively provided by first and second lasers.

24. An apparatus as claimed in claim 23, comprising a first diaphragm in said first beam and a second diaphragm in said second beam, said second diaphragm having a smaller diameter than said first diaphragm.

25. An apparatus as claimed in claim 16, further comprising a counter for counting the number of laser pulses to provide a controlled sequence of laser pulses on the sample.

26. An apparatus as claimed in claim 16, further comprising a lens for focusing second beam in the center of the bottom of said crater.

27. An apparatus as claimed in claim 16, further comprising an arrangement for ensuring that said first and second beams are substantially concentric.

28. An apparatus as claimed in claim 16, wherein said detector is an optical spectrometer.

29. An apparatus as claimed in claim 28, wherein said optical spectrometer comprises an enhanced gated photodiode array.

30. An apparatus as claimed in claim 28, wherein said optical spectrometer comprises an enhanced charge coupled devices.

31. An apparatus as claimed in claim 28, wherein said optical spectrometer comprises an array of individually positioned photomultipliers.

32. An apparatus as claimed in claim 16, wherein said depth profile evaluator, comprises an optical profilometer selected from the group consisting of: a confocal microscopy measurement device, a laser triangulation device, and an interferometer using a short coherence length light source.

* * * * *